US005736315A

United States Patent [19]
Fields et al.

[11] Patent Number: 5,736,315
[45] Date of Patent: Apr. 7, 1998

[54] METHODS AND COMPOSITIONS FOR DETECTING ANTI-HEPATITIS E VIRUS ACTIVITY

[75] Inventors: Howard A. Fields, Marietta; Michael O. Favorov; Yuri E. Khudyakov, both of Atlanta, all of Ga.

[73] Assignee: National Institute of Health, Bethesda, Md.

[21] Appl. No.: 965,667

[22] Filed: Oct. 21, 1992

[51] Int. Cl.[6] .................... C12Q 1/70; G01N 33/576; C07K 14/08

[52] U.S. Cl. .................. 435/5; 436/820; 530/326; 530/328

[58] Field of Search .......................... 530/326, 328; 436/806, 820; 435/69.3, 5

[56] References Cited

FOREIGN PATENT DOCUMENTS

WO 91/15603  10/1991  WIPO.
WO93/14116  7/1993  WIPO.

OTHER PUBLICATIONS

Goldsmith et al. *The Lancet* 339:328–331, 1992.
Tam et al. *Virology* 185:120–131, Nov. 1991.
Yarbough et al. *J. Virol.* 65:5790–5796, Aug. 1991.
Ichikawa et al. *Microbiol. Immunol.* 35(7):535–543, Apr. 1991.
Reyes et al. *Gastroenterologia Japonica* 26(3):142–147, 1991.
Reyes et al. Viral Hepatitis C, D and E *Elsevier Sci. Pub. B.V. (Biomed. Div.)*, chapter 43, pp. 237–245, 1991.
Reyes et al. *Science* 245:1335–1339, Mar. 1990.
Bradley et al. *Proc. Natl. Acad. Sci. USA* 84:6277–2681, May 1987.
Kaur et al., Human linear B–cell epitopes encoded by the hepatitis E virus include determinants in the RNA–dependent RNA polymerase. Proc. Natl. Acad. Sci. 89:3855–3858, 1992.
Favorov et al., Abstract #1662, *Abstracts of the 1992 ICAAC*, "Peptide EIA for detection of antibody to hepatitis E virus," p. 388.
Dawson et al., *Journal of Virological Methods* 38:175–186 (1992).

*Primary Examiner*—Marian C. Knode
*Assistant Examiner*—Donna C. Wortman
*Attorney, Agent, or Firm*—Jones & Askew, LLP

[57] ABSTRACT

The present invention provides antigenic peptides and polypeptides of hepatitis E virus. Also provided are mixtures of conjugated and unconjugated peptides of the present invention. Methods of detecting hepatitis E viral infection in a subject using the peptides and peptide mixtures of the present invention are also contemplated.

19 Claims, 3 Drawing Sheets

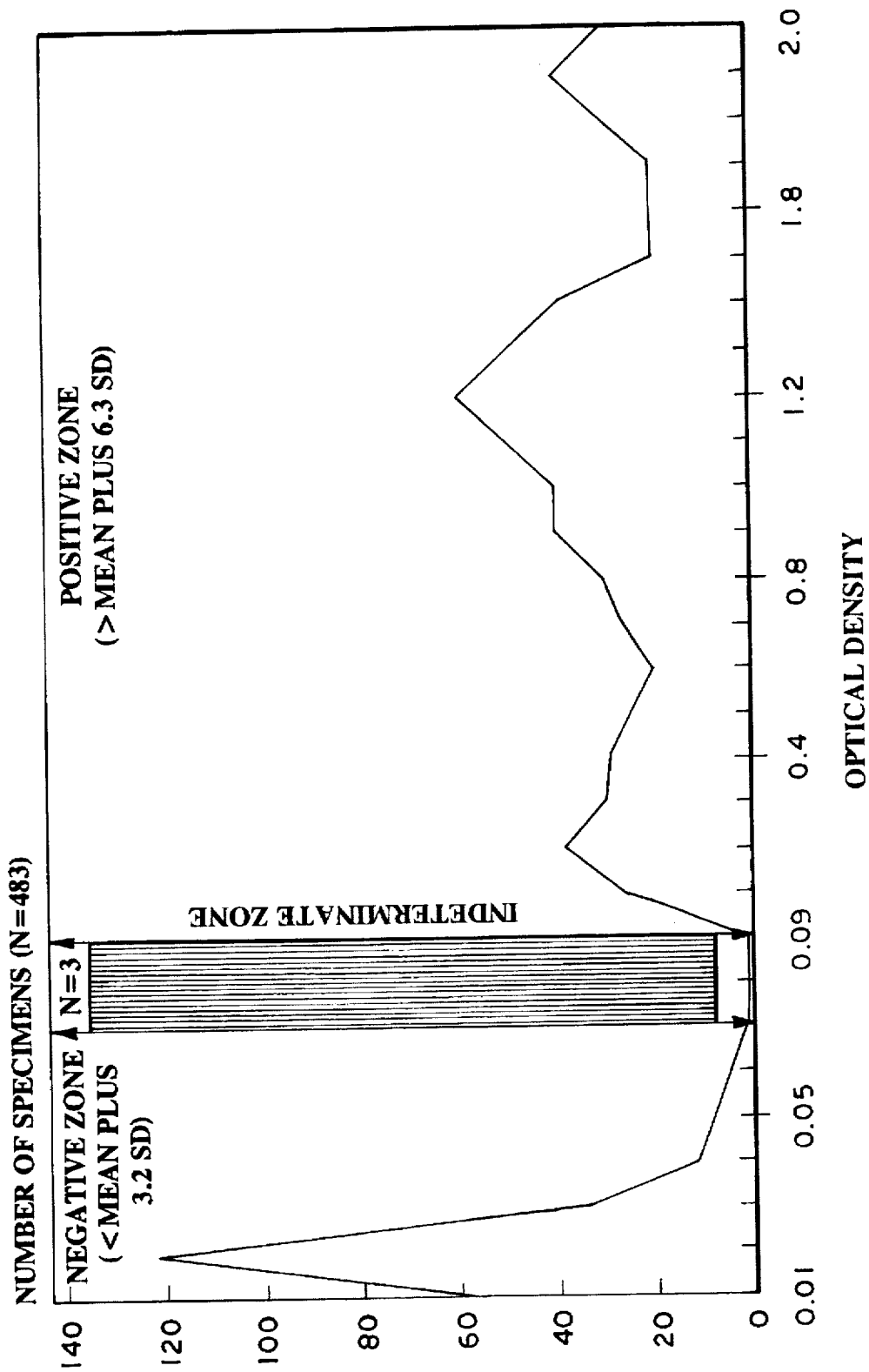

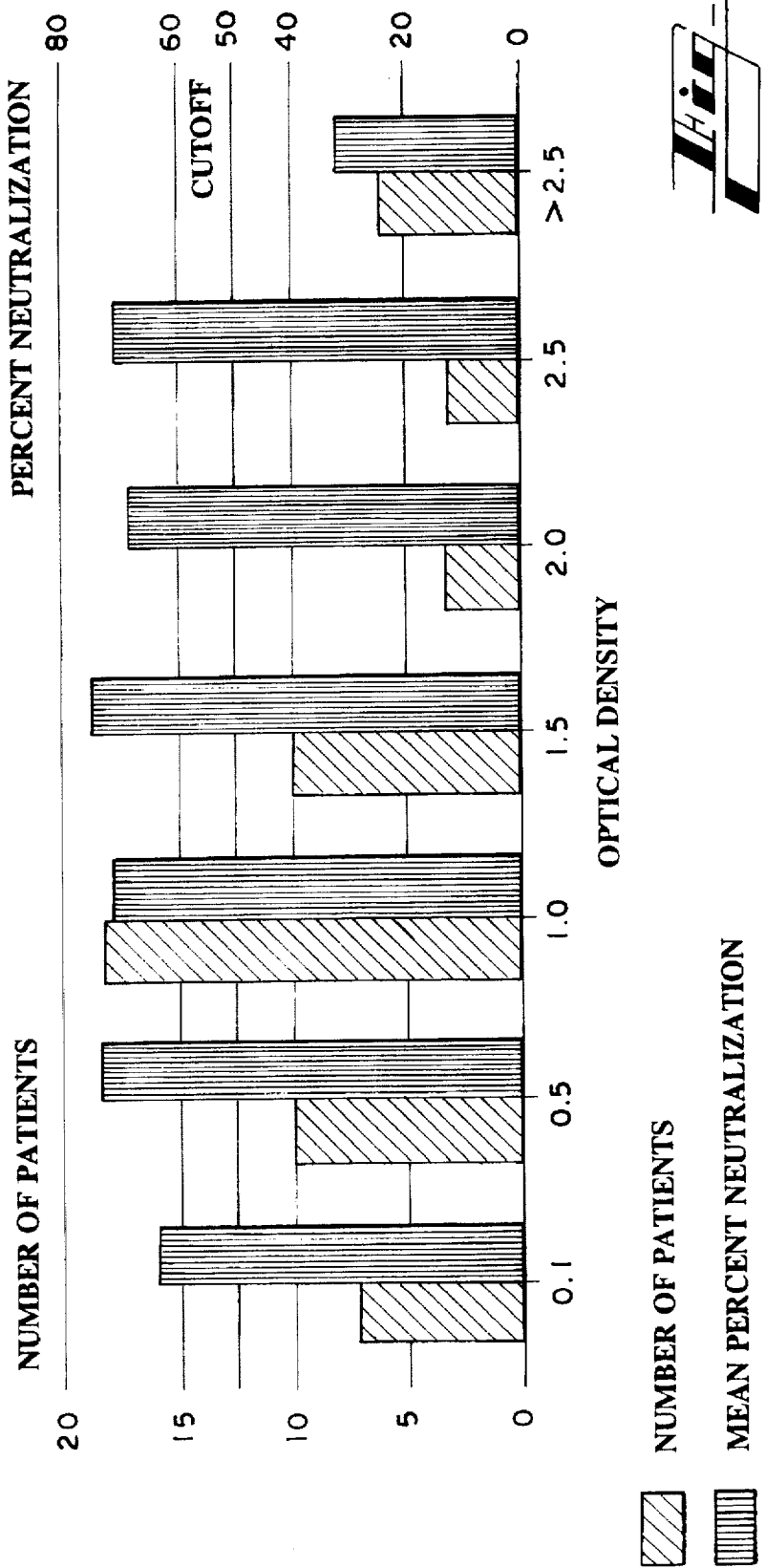

METHODS AND COMPOSITIONS FOR DETECTING ANTI-HEPATITIS E VIRUS ACTIVITY

BACKGROUND OF THE INVENTION

1. Field of the Invention

The invention pertains to methods and compositions for detecting anti-hepatitis E virus activity in a subject. The compositions include antigenic peptides of hepatitis E virus and mixtures of antigenic peptides of hepatitis E virus. The methods include serologic diagnosis of hepatitis E viral infection using the peptides and peptide mixtures of this invention.

2. Background Art

Hepatitis E virus (HEV) is a recently discovered agent of enterically transmitted non-A, non-B hepatitis (ET-NANB). The disease remains a serious problem in many developing countries. Unlike other agents of viral hepatitis, HEV infection is often associated with high mortality rates in infected pregnant women.

The first reported outbreak of ET-NANB hepatitis occurred in New Delhi, India in 1955. However, only after serologic tests for IgM anti-hepatitis A virus became available to exclude hepatitis A virus as the cause, was this very large outbreak recognized as ET-NANB hepatitis. Since that time epidemics of ET-NANB infection have been documented in many countries.

Until recently, the diagnosis of ET-NANB hepatitis outbreaks could only be based upon the absence of serologic markers of hepatitis A virus (HAV) and hepatitis B virus (HBV). Subsequently, specific tests for the detection of the ET-NANB hepatitis were based upon immune electron microscopy (IEM), in which a small volume of a stool suspension from acutely infected individuals is incubated with acute- or convalescent-phase sera and examined by electron microscopy (Bradley et al. *PNAS USA* 1987;84:6277–6281, 1987). IEM, thus identified 27–32 nm virus-like particles using acute and convalescent phase sera as the source of antibody. However, since most clinical specimens do not contain sufficient virus-like particles to visualize using IEM, this method is not useful for clinical or epidemiological analysis.

More recently, Reyes et al. (*Science* 247:1335–1339, 1990) successfully isolated and sequenced a partial cDNA clone from HEV. The HEV genome has subsequently been characterized as an RNA positive strand virus with an organization similar to Caliciviruses. Three open reading frames (ORF) have been identified (Tam et al. *Virology,* 185:120–131, 1991). Two type-common HEV epitopes were identified in proteins encoded by ORF2 and ORF3 (Reyes et al. *Gastroenterologia Japonica* 26 (suppl.3): 142–147, 1991b; Ichikawa et al. *Immunol.* 35:535–543, 1991). Both are localized at the C-terminus of their respective proteins. These epitopes were expressed as hybrid proteins with beta-galactosidase or glutathione-S-transferase and were recognized in an enzyme immunoassay by antibodies from acute- and convalescent-phase sera obtained from experimentally infected cynomologus macaques (Reyes et al., in "Viral hepatitis C,D,E", T. Shikata, R. H. Purcell, T. Uchida (Eds.) Elsevier Science Publishers, NY, pp. 237–245, 1991a) or humans (Goldsmith et al., *Lancet* 339:328–331, 1992). These hybrid proteins have the disadvantage that the chimeric part of protein can negatively influence folding. Furthermore, individuals may have antibodies expressed to these sequences.

ORF2 has been suggested to be responsible for the expression of the HEV structural protein(s) (Tam et al., 1991). In addition, the recombinant polypeptide containing the C-terminal half of the protein has been shown to be an important diagnostic reagent for the detection of anti-HEV activity in patients infected with HEV.

Reyes et al. (1991a) demonstrated that a short fragment of the C-terminal region of the protein encoded by ORF3, obtained by expression of DNA derived from the HEV genome of the Burma strain did not react with sera from cynomologous macaques infected with the Mexico strain of HEV. Conversely, expressed recombinant protein derived from the Mexico strain did not react with sera from macaques infected with the Burma strain of HEV (Yarbough et al. *J. Virol.* 65:5790–5797, 1991). Sequence comparison of the two strains at the C-terminal region of ORF3 revealed a 78% homology (Yarbough et al., 1991). Furthermore, there appear to be type-common viral epitopes that are shared by divergent geographic isolates from Asia and North America (Yarbough et al. 1991; Goldsmith et al., 1992).

Thus, because of the lack of sensitivity and difficulty of performing the previously available tests, there exists a need for a rapid, simple and highly sensitive diagnostic test for HEV infection.

The present invention meets these needs by providing synthetic peptides and their use in a diagnostic test for the detection of antibodies to the hepatitis E virus. The present invention provides for the application of synthetic peptides in an immunodiagnostic assay for the detection of antibodies to HEV (anti-HEV).

SUMMARY OF THE INVENTION

The present invention provides antigenic peptides of HEV. For example the peptides of the present invention can consist of the amino acids contained in the amino acid sequences defined in the Sequence Listing by SEQ ID NOS: 1, 2, 3, 4, 5, 6, 7, 8, 9, 10, 11, 12 or 13. The peptides of the present invention can be unconjugated, or they can be conjugated to a carrier molecule that facilitates placement of the peptide on the solid phase. Also provided is a composition comprising at least four different peptides, wherein the peptides are defined in the Sequence Listing by SEQ ID NO:1, SEQ ID NO:2, SEQ ID NO:7, SEQ ID NO:8 and SEQ ID NO:9.

This invention further provides a method of using the composition of different peptides for detecting hepatitis E vital infection in a subject by contacting an antibody-containing sample from the subject with a detectable amount of the peptides and detecting the reaction of the peptides and antibody specifically reactive therewith, the reaction indicating the presence of hepatitis E infection.

BRIEF DESCRIPTION OF THE FIGURES

FIG. 2 shows the frequency distribution of anti-HEV activity; and

FIG. 3 shows the results of a neutralization test using sera which initially tested positive and yielded optical density values from 0.1 to greater than 2.5.

DETAILED DESCRIPTION OF THE INVENTION

Antigen

Figure 1:
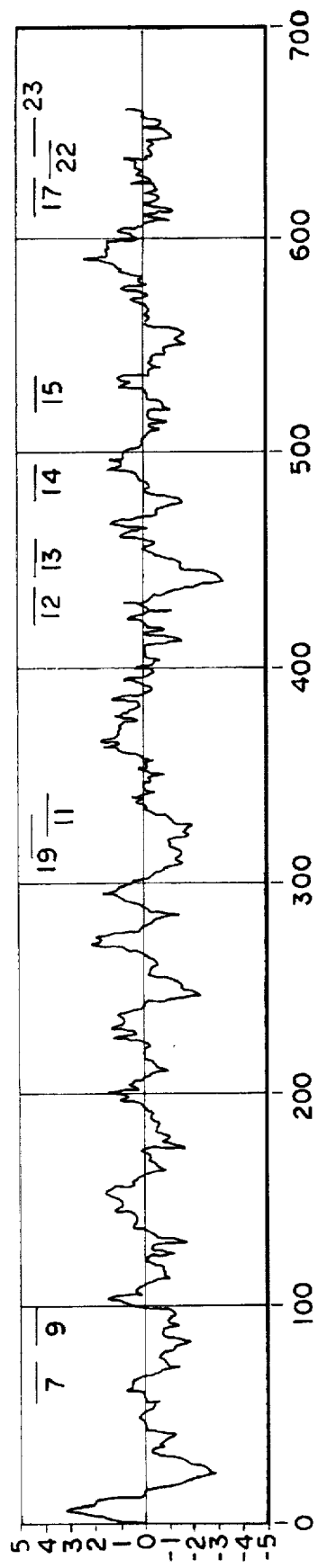
FIGS. 1A and 1B show hydropathy plots of the proteins encoded by HEV ORF2 (A) and ORF3 (B), and the localization of sequences selected for the synthesis of peptides.
Figure 1:
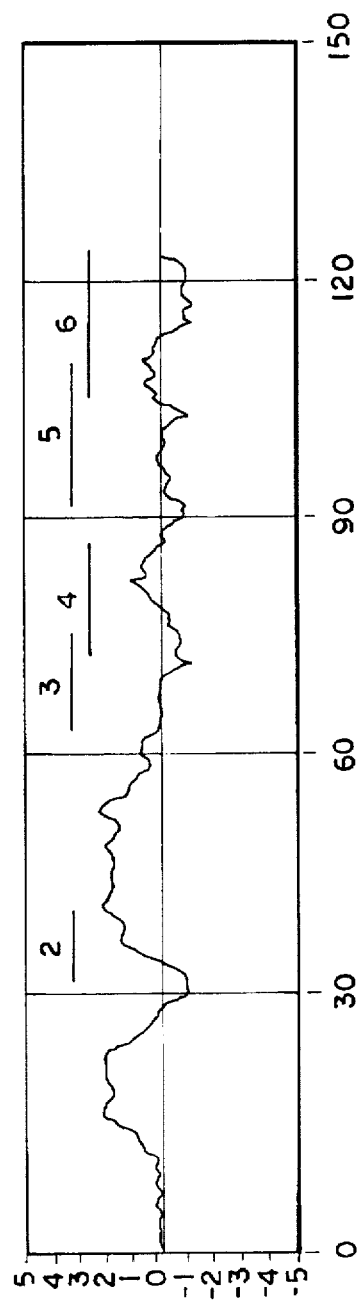
Figure 1:

The present invention provides antigenic polypeptide fragments or peptides of HEV. The peptides generally exist in a purified form. As used herein, "purified" means the peptide is essentially free of naturally occurring contaminants. The purified antigenic HEV peptides or polypeptides of the present invention are also referred to herein as "the antigen" or "the HEV antigen" and are designated interchangeably by either peptide number or SEQ ID NO (Tables 1 and 2).

The peptides of the present invention can consist essentially of the amino acids contained in the amino acid sequences defined in the Sequence Listing by SEQ ID NOS: 1, 2, 3, 4, 5, 6, 7, 8, 9, 10, 11, 12 or 13. Thus, the peptides of the invention have the same general sequence as found in the Sequence Listing. The peptides of the present invention can be unconjugated, or they can be conjugated to a carrier molecule that facilitates placement of the peptide on the solid phase. A carrier protein is one to which synthetic peptides can be conjugated and which will not react with antibodies in human serum. An example of such a carrier is bovine serum albumin (BSA).

Once the amino acid sequence of the antigen is provided, it is possible to synthesize, using the methods taught herein and standard peptide synthesis techniques, peptide fragments chosen to be homologous to immunoreactive regions of the antigen and to modify these fragments by inclusion, deletion or modification of particular amino acid residues in the derived sequences. Thus, synthesis or purification of an extremely large number of peptides derived from the antigen is possible.

Alternatively, an antigenic peptide can be isolated from the whole antigen by chemical or mechanical disruption. The purified peptides thus obtained can be tested to determine their antigenicity and specificity by the methods taught herein. An immunoreactive peptide is defined as an amino acid sequence of at least about 5 consecutive amino acids derived from the antigen amino acid sequence.

The peptide/polypeptide fragments of the present invention can also be recombinant proteins obtained by cloning nucleic acids encoding the polypeptide in an expression system capable of producing the antigenic peptide/polypeptide.

The amino acid sequences of the present peptides/polypeptides can contain an immunoreactive portion of HEV antigen attached to sequences designed to provide for some additional property, such as solubility as taught herein. The amino acid sequences of an HEV antigen can include sequences in which one or more amino acids have been substituted with another amino acid to provide for some additional property, such as to remove/add amino acids capable of disulfide bonding to increase the reactivity of an epitope by providing a more rigid secondary structure, to increase its bio-longevity or to alter its cytotoxicity or to prevent infection. In any case, the peptide must posses immunoreactivity and immunogenicity.

Peptide Mixtures

The present invention also provides mixtures (compositions) of the peptides provided herein as illustrated, for example, by mixtures 5, 7 and 9 described in the Example 2. In addition to the individual peptides, the mixtures of the present invention can also be referred to herein as "the antigen" or "the HEV antigen." As with the individual peptides, the mixtures of this invention can comprise conjugated peptides, unconjugated peptides or both. Furthermore, the conjugated peptides of the invention can be amounts of an individual peptide conjugated to a carrier (for example, mixture 7) or amounts of different peptides conjugated to a single carrier (for example, mixture 9). The mixtures, as well as the individual peptides, can be attached or bound to a substrate (solid phase).

Specifically, the present invention provides a composition comprising at least four different peptides, wherein the peptides have a sequence which consists essentially of the amino acids contained in the amino acid sequences defined in the Sequence Listing by SEQ ID NO:1, SEQ ID NO:2, SEQ ID NO:8 and SEQ ID NO:9. The peptides of this mixture can be conjugated, individually or as a mixture, to a carrier and can then be bound to a substrate. When this composition further comprises the peptide consisting essentially of the amino acids contained in the amino acid sequence defined in the Sequence Listing by SEQ ID NO:7, mixture 7 is provided.

Also provided is a composition comprising at least eight peptides, wherein the peptides have a sequence which consists essentially of the amino acids contained in the amino acid sequences defined in the Sequence Listing by SEQ ID NO:1, SEQ ID NO:2, SEQ ID NO:5, SEQ ID NO:6, SEQ ID NO:8, SEQ ID NO:9, SEQ ID NO:10 and SEQ ID NO:11. The peptides of this mixture are conjugated, individually or as a mixture, to a carrier and can then be bound to a substrate.

Other mixtures of peptides of the present invention can, for example include the following:

Peptide 2 and one or more of peptides 3, 5, 6, 11, 12, 13, 22, 23, 28, 29, 33 and 40; Peptide 3 and one or more of peptides 2, 5, 6, 11, 12, 13, 22, 23, 28, 29, 33 and 40Peptide 5 and one or more of peptides 2, 3, 6, 11, 12, 13, 22, 23, 28, 29, 33 and 40; Peptide 6 and one or more of peptides 2, 3, 5, 11, 12, 13, 22, 23, 28, 29, 33 and 40; Peptide 11 and one or more of peptides 2, 3, 5, 6, 12, 13, 22, 23, 28, 29, 33 and 40; Peptide 12 and one or more of peptides 2, 3, 5, 6, 11, 13, 22, 23, 28, 29, 33 and 40; Peptide 13 and one or more of peptides 2, 3, 5, 6, 11, 12, 22, 23, 28, 29, 33 and 40; Peptide 22 and one or more of peptides 2, 3, 5, 6, 11, 12, 13, 23, 28, 29, 33 and 40; Peptide 23 and one or more of peptides 2, 3, 5, 6, 11, 12, 13, 22, 28, 29, 33 and 40; Peptide 28 and one or more of peptides 2, 3, 5, 6, 11, 12, 13, 22, 23, 29, 33 and 40; Peptide 29 and one or more of peptides 2, 3, 5, 6, 11, 12, 13, 22, 23, 28, 33 and 40; Peptide 33 and one or more of peptides 2, 3, 5, 6, 11, 12, 13, 22, 23, 28, 29 and 40; and Peptide 40 and one or more of peptides 2, 3, 5, 6, 11, 12, 13, 22, 23, 28, 29 and 33. These peptides are shown individually in Tables 1 and 2.

Determining Antigenicity/Immunoreactivity

A method of selecting alternative peptides having immunoreactivity with an antibody reactive with the peptides of this invention is also provided. For example, such a method for determining the minimal sequence for immunoreactivity of a peptide having immunoreactivity with an antibody reactive with HEV includes the following steps: (a) modifying a peptide of the present invention; (b) contacting the modified peptide with a confirmed HEV positive serum sample from a subject; and (c) detecting the reaction of the modified peptide and anti-HEV antibody, the reaction indicating that the modified peptide has immunoreactivity with HEV. An example of this method, which can be applied to the other peptides of the present invention, is illustrated in Example 1. Any of the peptides of the invention can likewise be modified.

Determining Immunogenicity

The purified peptide/polypeptide fragments thus obtained can be tested to determine their immunogenicity and specificity. Briefly, various concentrations of a putative immunogenic ally specific peptide are prepared and administered to an animal and the immunological response (i.e., the production of antibodies) of an animal to each concentration is determined. The amounts of antigen administered depend on the subject, e.g. a human or other susceptible animal, the condition of the subject, the size of the subject, etc. Thereafter an infection-susceptible animal so inoculated with the antigen can be exposed to the virus to test the potential vaccine effect of the specific immunogenic peptide. The specificity of a putative immunogenic peptide can be ascertained by testing sera or other fluid from the inoculated animal for cross reactivity with other closely related viruses. Alternatively, the immunogenicity can be tested in an in vitro method using serum from the immunized animal to attempt to neutralize infectious virus, which can then be added to cell culture to determine if the peptide elicited neutralizing antibodies.

Recombinant Mosaic Proteins

Because the present invention provides the amino acid sequences of antigenic peptides and their nucleic acid coding sequences in the HEV genome (Yarbough et al., 1991), a recombinant mosaic protein can be produced comprising a plurality of the peptides of the present invention.

The protein can include the epitopes of peptides 5, 6, 22, 23, 33 and 40, among others, and can also include additional amino acids that do not substantially affect the antigenicity of the protein. This mosaic protein is highly sensitive and specific because of the absence of extraneous amino acids that can interfere with the presentation of the epitopes. It is contemplated that the mosaic proteins of this invention can be used, as described herein, for diagnostic tests and vaccines. The currently preferred method of expressing the mosaic protein is by means of vector-host expression systems.

Vectors and Hosts

A vector comprising the nucleic acids of the present invention is also provided. The vectors of the invention can be in a host capable of expressing the antigen. Making and using such vectors and hosts, using the teachings of the present invention, is within the level of skill of those in the art.

There are numerous *E. coli* expression vectors known to one of ordinary skill in the art useful for the expression of the antigen. Other microbial hosts suitable for use include bacilli, such as *Bacillus subtilus*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences, for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast. The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either Gentamicin or methotrexate resistance for use as selectable markers. The antigen and immunoreactive peptide coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation can be used for other cellular hosts.

Alternative vectors for the expression of antigen in mammalian cells, similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted DNAs in mammalian cells (such as COS7).

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Polynucleotides encoding a variant peptide/polypeptide can include sequences that facilitate transcription (expression sequences) and translation of the coding sequences such that the encoded peptide/polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Purified Antibodies

A purified monoclonal antibody specifically reactive with the antigen is also within the scope of the invention. The antibodies can be specifically reactive with a unique epitope of the antigen or they can also react with epitopes of other organisms. The term "reactive" means capable of binding or otherwise associating nonrandomly with an antigen. "Specifically reactive" as used herein describes an antibody or other ligand that does not cross react substantially with any antigen other than the one specified, in this case, the HEV antigen. Antibodies can be made as described in Harlow and Lane (Antibodies; A Laboratory Manual, Cold Spring Harbor laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen DNA clone libraries for cells secreting the antigen. Those positive clones can then be sequenced as described in the Examples or by other methods (see, for example, Kelly et al., Bio/Technology 10:163–167, 1992 and Bebbington et al., Bio/Technology 10:169–175, 1992). Purified nonhuman, preferably mammalian, polyclonal antibodies reactive with the HEV antigenic peptides provided herein are also contemplated. The polyclonal antibody can also be obtained by the standard immunization and purification protocols (Harlow and Lane, 1988).

The antibody can be bound to a substrate or labeled with a detectable moiety or both bound and labeled. The detectable moieties contemplated with the composition of the present invention are those listed below in the description of the diagnostic methods, including fluorescent, enzymatic and radioactive markers.

Serological Detection (Diagnosis) Methods
Detecting Antibody with Antigen

The present invention provides a method of detecting HEV infection in a subject, comprising the steps of contacting an antibody-containing sample from the subject with a detectable amount of an HEV antigenic peptide or peptide mixtures of the present invention, under suitable reaction conditions, and detecting the reaction of the peptide and the antibody specifically reactive therewith, the reaction indicating the presence of HEV or previous infection with HEV.

Detectable amounts of the present peptides can be determined empirically once their sequence and antigenicity are provided. The concentration of an individual peptide in a mixture can also be determined empirically. Peptides with higher conjugation efficiency will be added to the mixtures in lower concentrations than less efficiently conjugated peptides. Examples of detectable concentrations of peptides combined in a mixture are provided in mixtures 5, 7, 9 described in Example 2. For instance mixtures 7 and 9 are compositions in which, prior to the conjugation step, the preferred concentration of the peptide defined by SEQ ID NO:1 is about 8 micrograms per milliliter, the concentration of the peptide defined by SEQ ID NO:2 is about 14 micrograms per milliliter, the concentration of the peptide defined by SEQ ID NO:7 is about 4 micrograms per milliliter, the concentration of the peptide defined by SEQ ID NO:8 is about 4 micrograms per milliliter, and the concentration of the peptide defined by SEQ ID NO:9 is about 20 micrograms per milliliter.

It is also understood that ranges of concentration ratios including the above values can be determined that are also antigenically effective and detectable. For example, the concentration ratio of the peptides defined by SEQ ID NO:1, SEQ ID NO:2, SEQ ID NO:7, SEQ ID NO:8 and SEQ ID NO:9 can be about 8:14:4:4:20. The determination of such effective ratios should also take into consideration the ratio of peptide to carrier as taught in Example 2.

Detecting Antigen with Antibody/Ligand

One example of the method of detecting HEV possessing the antigen is performed by contacting a fluid or tissue sample from the subject with an amount of a purified antibody specifically reactive with the antigen, and detecting the reaction of the ligand with the antigen. It is contemplated that the antigen will be on an intact HEV virion, on HEV-infected cells expressing the antigen, or will be fragments of the antigen. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as cerebrospinal fluid, blood, bile, plasma, serum, saliva and urine. Other possible examples of body fluids include sputum, mucus and the like.

ELISA

Enzyme immunoassays such as immunofluorescence assays (IFA), enzyme linked immunosorbent assays (ELISA) and immunoblotting can be readily adapted to accomplish the detection of the HEV antibodies. An ELISA method effective for the detection of the antibodies can, for example, be as follows: (1) bind the antigen to a substrate; (2) contact the bound antigen with a fluid or tissue sample containing the antibody; (3) contact the above with a secondary antibody bound to a detectable moiety which is reactive with the bound antibody (e.g., horseradish peroxidase enzyme or alkaline phosphatase enzyme); (4) contact the above with the substrate for the enzyme; (5) contact the above with a color reagent; (6) observe color change.

Competitive Inhibition Assay

Another immunologic technique that can be useful in the detection of HEV or previous HEV infection utilizes monoclonal antibodies (MAbs) for detection of antibodies specifically reactive with HEV antigen. Briefly, sera from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

Micro-Agglutination Assay

A micro-agglutination test can also be used to detect the presence of HEV in a subject. Briefly, latex beads, red blood cells or other agglutinable particles are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or by spectrophotometer. In a modification of the above test, antibodies specifically reactive with the antigen can be bound to the beads and antigen in the tissue or body fluid thereby detected.

Sandwich Assay/Flow Cytometry/Immunoprecipitation

In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides HEV antigen for the detection of HEV or previous HEV infection other serological methods such as flow cytometry and immunoprecipitation can also be used as detection methods.

In the diagnostic methods taught herein, the antigen can be bound to a substrate and contacted by a fluid sample such as blood, serum, urine or saliva. This sample can be taken directly from the patient or in a partially purified form. In this manner, antibodies specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecifically with the ligand or reacted antibody, will be selected for its ability to react with multiple sites on the primary antibody. Thus, for example, several molecules of the secondary antibody can react with each primary antibody, making the primary antibody more detectable.

Detectable Moieties

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change).

Detecting Disease

Because the purified HEV antigen provided herein is associated with disease, the present invention also provides a method of detecting HEV associated disease syndrome in a subject. The method can be accomplished according to the methods set forth above for the detection of HEV antigen and antibodies specifically reactive therewith. The presence of the HEV antigen or anti-HEV antibodies indicates the presence of disease syndrome in the subject.

The present invention also provides a method for diagnosing the acute phase of hepatitis E infection in a subject by contacting an antibody-containing sample from the subject with a detectable amount of a peptide or mixture having a relatively rapidly decaying immune response and detecting the reaction of the peptides and antibody specifically reactive therewith, the reaction indicating acute hepatitis E infection.

Vaccines

The antigen of this invention can be used in the construction of a vaccine comprising an immunogenic amount of the antigen and a pharmaceutically acceptable carrier. The vaccine can be a peptide of the present invention or the peptide bound to a carrier or a mixture of bound or unbound peptides or an epitope specific to the antigen or it can be potentially reactive with antibodies to other infectious agents. The vaccine can then be used in a method of preventing HEV infection.

Immunogenic amounts of the antigen can be determined using standard procedures. Briefly, various concentrations of a putative specific immunoreactive peptides or polypeptides are prepared, administered to an animal and the immunological response (e.g., the production of antibodies or cell-mediated response) of an animal to each concentration is determined.

The pharmaceutically acceptable carrier in the vaccine of the instant invention can comprise saline or other suitable carriers (Arnon, R. (Ed.) Synthetic Vaccines I:83–92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic. Thus, the invention provides methods of preventing or treating an HEV infection and the associated disease by administering the vaccine to a subject.

Antibody-Detecting Kit

The diagnostic kit of the present invention can be used to detect the presence of a primary antibody specifically reactive with HEV or an antigenic peptide thereof. The kit can include the HEV antigen of the present invention bound to a substrate, a secondary antibody reactive with the antibody specifically reactive with the HEV antigen and a reagent for detecting a reaction of the secondary antibody with the primary antibody. Such a kit can be an ELISA kit and can comprise the substrate, antigen, primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

Antigen-Detecting Kit

The present invention provides a kit for the diagnosis of infection by strains of HEV possessing the HEV antigen. Particularly, the kit can detect the presence of HEV antigen or an immunoreactive peptide thereof specifically reactive with an antibody. The kit can include an antibody bound to a substrate, a secondary antibody reactive with the antigen and a reagent for detecting a reaction of the secondary antibody with the antigen. Such a kit can be an ELISA kit and can comprise the substrate, primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

The particular reagents and other components included in the diagnostic kits of the present invention can be selected from those available in the art in accord with the specific diagnostic method practiced in the kit. Such kits can be used to detect the antigen in tissue and fluid samples from a subject.

The following examples are intended to illustrate, but not limit, the invention. While they are typical of those that might be used, other procedures known to those skilled in the art may be alternatively employed.

EXAMPLE 1

Selection and Synthesis of Antigenic Peptides
Sequence Selection.

Three criteria were used to select sequences for putative antigenic peptides: hydrophilicity, flexibility, and secondary structure. Prediction of hydropathy plots (Kyte, J. and Doolitle, R. F. *J. Mol. Biol.* 157:105–132, 1982) and secondary structure (Chou, P. Y. and Fasman, G. D. *Ann.Rev. Biochem.* 47:251–276, 1978) of proteins was accomplished using computer analysis (PROSIS; Hitachi Software Engineering Co., Ltd.). Segmental flexibility of proteins along a chain was analyzed by a method described by Karplus and Schulz (*Naturwissenschaften* 72:212–213, 1985). In addition, the secondary structure of proteins was predicted by the method developed by Ptitsin and Finkelstein (*Biopolymers* 22:15–25, 1983).

Sequences of the synthetic peptides selected to be synthesized are shown in Tables 1 and 2. Most of the peptides chosen for synthesis contain hydrophilic and flexible sequences represented in the predicted secondary structure as beta-turns or random coils (Tables 1 and 2). Synthetic peptides covering almost the entire ORF3 protein were prepared with the exception of two very strong hydrophobic regions in the N-terminal half of the molecule. Using additional criteria (Eisenberg et al. *J. Mol. Biol.* 179:125–142, 1984; Klein et al. *Biochem. Biophys. Acta* 815:468–476, 1985), these two regions may be predicted to be transmembrane alpha-helices. Hydropathy plots are important in selecting antigenic peptides, because hydrophobic regions usually have the potential to be represented as α-helices and may function as transmembrane regions that may not be available for interaction with the immune system. Strong hydrophobic potential of the N-terminal region suggests the protein could be associated with cellular membranes possibly playing a role in excretion of the HEV particles. Although HE virions contain no known traces of lipids, existence of a strong hydrophobic region at the N-terminus of the structural protein(s) encoded by the large ORF2 additionally indicates a possible role of membranes in the morphogenesis of HEV. Taking this finding into consideration, a short sequence between these two hydrophobic regions was selected for synthesis in addition to peptides spanning the C-terminal relatively hydrophilic region of the ORF3 protein. This short hydrophilic sequence may be a loop located between these two transmembrane domains. If this region is exposed, it could be a strong antigenic epitope of the ORF3 protein.

Due to the length of ORF2, synthetic peptides were selected using additional considerations. The whole N-terminal half of the protein contains high concentrations of Arg and Lys. These amino acids have a potential to be bound to nucleic acids suggesting that in virion particles this region may have an internal localization. Nonetheless, a few peptides were selected from the hydrophilic and flexible region of the N-terminal half of the protein for synthesis with the knowledge that internal proteins of viral particles such as HBV, HDV, or HCV have been important diagnostic reagents.

Synthesis of Peptides.

Peptides were synthesized by FMOC-chemistry (Barany and Merrifield, 1980) on an ABI Model 430A automated peptide synthesizer (Applied Biosystems, Inc., Foster City, Calif.) or on an ACT Model MPS 350 multiple peptide synthesizer (Advanced Chemtech, Louisville, Ky.) according to the manufacturer's protocols. Protocols have been described previously and are available as FastMoc™ cycles (Applied Biosystems, Inc. 1990, FastMoc™ chemistry: HBTU activation in peptide synthesis on the Model 430A Peptide Synthesizer User Bulletin 32; and HBTU activation in peptide synthesis on the Model 431A Peptide Synthesizer User Bulletin 33). There are two scales, 0.10 and 0.25 mmol, with total cycle times of 20 and 60 min, respectively. The Fmoc deprotections were done with piperidine in N-methylpyrrolidone (NMP), and the resin was washed with NMP. In both scales, 1.0 mmol of Fmoc-amino acid was dissolved in NMP, and 1 mmol of 0.45M HBTU(2-(H-benzotriazol-1-yl)-1,1,3,3,-tetramethyluronium hexafluorophosphate)/0.45M HOBt(1-Hydroxybenzotriazole) in DMF(N,N-dimethylformamide). The dissolved Fmoc-amino acid was transferred to the reaction vessel along with 1.7–2.0 mmol of DIEA (diisopropylethylamine) and allowed to react with the peptide resin for approximately 10 min with the 0.10 mmol cycles and 30 min with the 0.25 mmol cycles.

Peptides were cleaved by placing 10 mg of peptide resin in a test tube containing 200 μl of either 5% thioanisole/ 2.5% ethanedithiol/2.5% $H_2O$/90% TFA or 2.5% ethanedithiol/5% $H_2O$/92.5% TFA and mixing for 1 h. Approximately 3.5 ml of $H_2O$ were then added, the mixture was extracted 3–5 times with 2–3 ml of t-butyl methyl ether, and the aqueous layer was filtered. Any insoluble peptide was dissolved in the aqueous layer by addition of acetic acid, ammonium hydroxide or isopropanol, as appropriate before analyses.

After characterization by amino acid analysis, high performance liquid chromatography and capillary electrophoresis, peptides were used directly in enzyme immunoassay.

Antigenic Activity of the Peptides.

Initial analysis of the peptides (Tables 1 and 2) utilizing enzyme immunoassay (EIA) was performed on sera obtained from an outbreak in Central Asia (Table 3). All the samples from this collection were tested by western blot analysis recently developed for HEV infection and by the peptide EIA.

Sera.

Sera from outbreaks of enterically transmitted non-A, non-B hepatitis in Central Asia (1985), Mexico (1986), and Kenya (1991) were used to identify HEV-specific epitopes in proteins encoded by ORF2 and ORF3. As a negative control for this analysis, a collection of sera from humans with HAV, NCV, HBV, HDV markers of infection, or from normal blood donors were used.

Sera from viral hepatitis patients ages 1 to 67 years were collected from outbreaks of vital hepatitis between 1984 and 1992 in geographically distinct regions of the world (Central Asia and Mexico). Whenever possible sera was obtained from infected patients beginning at the onset of jaundice through the 27th day of jaundice. In addition, convalescent sera was obtained from 1–24 months after hospital discharge. All sera were originally diagnosed as NANBH by serologic exclusion of markers for HAV, HBV, and HCV using commercially available tests (Preparat, Nizny Novgorod, Russina; Abbott Laboratories, North Chicago, Ill.). Reagents: Affinity purified goat anti-human IgG conjugated to horseradish peroxidase (HRP) was obtained from TAGO (Burlingame, Calif.) and used at a dilution of 1:40,000. To confirm the specificity of this detector molecule, monoclonal antibody specific for human IgG or for IgM conjugated to HRP was used at a dilution of 1:2000 and Western Blot Assay.

All sera were tested for anti-HEV activity by western blot that was carried out according to Favorov et al. (*J. Med. Virol.* 36:246–250, 1992).

Recombinant chimeric proteins, C2 and C2-1, containing the N-terminal region of trypE (37 kDa) and the C-terminal half (46.8 kDa) of the polypeptide encoded by ORF2 (Purdy et al., 1992) were used for the development of a Western blot (WB) diagnostic test to detect IgG and IgM class antibodies to the HEV.

Recombinant fusion protein C2 (83.8 kDa) and the fusion protein C2-1 (49.5 kDa) were expressed in *Escherichia coli* and lysates containing these proteins were obtained as described previously (Purdy et al., 1992). C2 and C2-1 lysates were mixed and separated electrophoretically in 8% or 11% sodium dodecyl sulfate (SDS)-polyacrylamide gels (Purdy et al., 1992). Separated proteins were transblotted to BAS 83 nitrocellulose (Scheicher & Schuell, Keene, N.H.) using a TE70 SemiPhor (Hoefer, San Francisco, Calif.) as described previously (Purdy et al. 1992). Two millimeter strips were cut and incubated for 16–20 hr at 20° C. in 50 mM Tris-HCl, pH 7.5, containing 5 mM EDTA, 150 mM NaCl, 0.05% NP-40, 0.25% gelatin, and 1.0% bovine serum albumin (NET-BSA) prior to storage at 4° C. Strips could be stored in NET-BSA for 1–2 weeks at 4° C. or dried under vacuum and stored for longer periods.

Unknown serum specimens were diluted (minimum dilution 1:20) in NET buffer containing a 1% extract of an *E. coli* lysate without the recombinant plasmid and incubated for 2 hr at room temperature. Following incubation, the strips were washed in NET buffer three times for 10 min, and incubated with horseradish peroxidase (HRP) conjugated affinity purified detector antibodies. These included goat anti-human IgM and goat anti-human IgG (TAGO, Burlingame, Calif.; Sigma Chemical Co., St. Louis, Mo). The specificity of human immunoglobulin isotypes was confirmed with HRP conjugated murine monoclonal anti-human IgG and anti-human IgM (American Qualex, La Mirada, Calif.). The strips were then incubated in phosphate-buffered saline (PBS), pH 7.2, containing 100 mg of 3,3'-diaminobenzidine and 100 µl of $H_2O_2$ for color development.

To eliminate non-specific reactions, C2 and C2-1 proteins were individually located and excised from the polyacrylamide gel. These were eluted separately in 0.5M Tris-HCl buffer, pH 6.8, electrophoretically repurified in 8.5% SDS-polyacrylamide gels, transblotted, and tested with the serum specimens that gave non-specific reactions. In addition, to confirm conjugate immunoreactivity for each analysis, purified immunoglobulin heavy chains (gamma-specific and mu-specific, Chemicon, El Segundo, Calif.) were electrophoretically separated, transblotted, and immunostained separately.

This method for detecting HEV infection is not sensitive enough to detect a significant number of instances of acute or prior infection. Furthermore, the western blot method described is time consuming, because purification of the recombinant proteins is required before use.

Enzyme Immunoassay.

Microtiter wells (Immulon I, Dynatech Laboratories, Inc.) were adsorbed with 100 ul of synthetic peptides at a concentration of 5 ug per well. Human sera were diluted 1:50 in 0.1M PBS, pH7.5, containing 0.1% Tween 20 and 10% normal goat serum, and 100 ul were added to each well to capture antibodies reactive to the adsorbed peptides. To identify sera containing anti-peptide activity, affinity purified anti-human antibodies conjugated to horseradish peroxidase (HRP) (heavy-chain specific; TAGO, Inc., Burlingame, Calif., USA) were used.

The cutoff was statistically established to be three times the average negative control value.

Central Asia Epidemic

As shown in Table 3, four of 5 ORF3 specific peptides (2, 3, 5 and 6) and 4 of 12 ORF2 specific peptides (11, 12, 22 and 23) were reactive with most of the sera. All but one serum positive by western blot analysis were reactive in the EIA with one or more synthetic peptides. Peptides 5 and 6 seem to represent dominant antigenic epitopes, since these two peptides bind antibodies from almost all sera analyzed (97.5%). Only 1 of 40 western blot anti-HEV positive sera was not reactive with these peptides (Table 3).

Peptides 2, 3, 11, 12, 22 and 23 were reactive with approximately 30% of sera. Peptides 10, 13, and 14 (Table 3) displayed reactivity with both anti-HEV positive and negative sera. These peptides were considered non-specific. Thus, 8 immunoreactive regions (peptides 2, 3, 5, 6, 11, 12, 22 and 23) encoded by the large ORF2 and the small ORF3 were identified (Table 3).

Peptides 33 and 40 (Table 2) are also very immunoreactive. Peptide 33 reacted with 81% of the anti-HEV positive sera (data not shown). Peptide 40 is reactive with 45% of positive sera (data not shown). Both peptides are very important for the diagnosis of HEV infection. These two peptides can be included in the mixtures of the present invention (for example, mixture 9) to improve the sensitivity of the peptide EIA for the detection of an anti-HEV antibody.

Mexico Epidemic.

Synthesis of the majority of the present peptides, including 5 and 6, was based on the sequence of the Burma strain of HEV. Peptides 28 and 29 were selected and synthesized based on the Mexico strain sequence (Yarbough et al., 1991) at precisely the same location as 5 and 6, but with different sequences. Comparative analysis of peptides 5 and 6, and 28 and 29 demonstrated that there was no strict strain specificity for these peptides (Table 4).

Peptides 28 and 29 are reactive with sera from the Mexico outbreak in 1986 as expected; however, even combinations of peptides 5, 6, 22, 23, 28 and 29 did not identify all sera positive by western blot analysis or by fluorescent antibody blocking assay (Krawczynski and Bradley, 1989) from the Mexico outbreak (Table 4, sample 395). In the IFA, known infected tissue was contacted with unknown serum, washed, detector-labeled human anti-HEV IgG added, and observed for the presence of label. The same specimen (395) did not react with any peptide, however, it remains strongly reactive by western blot analysis and by IFA. Additionally, specimen 67 (Table 4) was anti-HEV negative by western blot analysis and IFA, but was reactive with peptides 5, 6 and 22.

Peptides 5 and 6 always reacted with the same set of sera; however, peptides 28 and 29 having the same location but based on the Mexican HEV strain sequence did not always react simultaneously with the same specimen. An epitope represented in peptide 28 appeared to be more immunoreactive than an epitope represented in peptide 29 (Table 4). Thus, there appears to be a difference in the primary structure of peptides 5 and 28, and 6 and 29 that may lead to changes in antigenic activity of these epitopes.

Kenya Epidemic.

When analyzing sera obtained from a recent outbreak in Kenya peptides 5, 6, 22, 23, 28, and 29 were tested against the sera. Among 93 sera chosen for peptide analysis, 24 sera were obtained from patients with reported jaundice within half a year (Table 5). The remaining 69 specimens were collected from people without a history of jaundice, but who lived in the same location where the outbreak occurred (Table 6). Initially, all sera were characterized by western blot analysis for anti-HEV activity and for the presence of IgM antibody to the hepatitis A virus (HAV) by EIA. All sera were negative for IgM anti-HAV activity (not shown).

Among sera from reported cases of jaundice, 23 were found anti-HEV positive by peptide EIA. Twenty-seven sera were found anti-HEV positive by western blot analysis among specimens obtained from individuals who had not reported jaundice within the last 6 months (Table 6).

Peptide 29 was found non-reactive with these sera from Kenya and peptide 28 was reactive with only a few samples. However, peptides 5 and 6 reacted with about 71% of sera from the reported cases of jaundice and 48.2% of sera found anti-HEV positive by western blot analysis. One specimen (138) from an individual with no history of jaundice was found specifically reactive with peptides 5 and 6 but not reactive by western blot analysis.

Peptides 22 and 23 were more reactive than 5 and 6. More than 95% of sera from patients with reported cases of jaundice was identified with both of these peptides. About 82% of sera from people with no history of jaundice positive by western blot analysis were also reactive with these peptides. Eight sera negative by western blot analysis were found to contain antibody activity specifically reactive with peptides 22 and 23. Thus, a combination of peptides 22 and 23 identified more anti-HEV positive sera than peptides 5 and 6. Individual peptides 22 and 23 used separately demonstrated stronger immunoreactivity than peptides 5 and 6. For example, peptide 22 reacted with 79.2% and 66.7% of sera, and peptide 23 with 79.2% and 63% of sera obtained from people who had reported jaundice or positive by western blot analysis for anti-HEV activity, respectively (compared with 70.8% and 48.2% for 5 and 6 mentioned above). Collectively, peptides 5, 6, 22, and 23 could identify all reported cases of HEV infection from the outbreak in Kenya in the synthetic peptide EIA. Western blot analysis was less sensitive compared with peptide EIA. Only one specimen (144) obtained from patients with jaundice was not identified as positive by western blot analysis (Table 5).

Many sera containing anti-HEV activity without jaundice may be due to either past HEV infections or due to asymptomatic HEV infections. Among reported cases with jaundice there were more examples of immunoreactivity against 4 different peptides than among cases without a history of disease. Peptides 5, 6 and 22, and 23 identified the same percent of patients among reported cases of the disease. However, peptides 5 and 6 were 2-fold less reactive with sera from the group not reported as jaundice cases (see Table 6). The humoral immune response to the antigenic epitopes of peptides 5 and 6 may decay faster than the epitopes of peptides 22 and 23. Thus peptides 5 and 6 can be used for the differential diagnosis of various stages of the HEV infection. Conversely, peptide 13 can detect antibodies in serum up to 3 years after acute infection.

Strain specificity is shown insofar as sera obtained from Mexico have a different pattern of interaction with the synthetic peptides compared with sera obtained from Central Asia or from Kenya (Table 3–6). There is only a 78% homology between the ORF3 protein region comprising 5 and 6, or 28 and 29 (Yarbough et al., 1991). With the Mexico sera, peptides 5 and 6 identified the same percent of positives as 28 and 29 (Table 2). However, with sera from Central Asia (data not shown) and from the Kenya outbreak, peptides 28 and 29 were less reactive as evidenced by a low percentage of sera positive for anti-HEV using these peptides. Thus, our data show that the Burma strain of HEV is related to a greater extent to the Kenya or Central Asia viruses than to the Mexico strain of HEV.

There are at least 4 antigenic regions in the protein encoded by ORF3 and at least 7 antigenic regions in the protein encoded by ORF2. Among 12 peptides selected for synthesis from the structural protein(s) only 4 (33%) were specifically reactive with sera from HEV infected individuals.

Identification of Minimal Antigenic Sequence.

A set of peptides of 6 amino acids long (or 7, or 8 etc.) must be synthesized. These peptides are overlapped by 5 aa long regions (or 6 for 7 aa long peptides, etc.) and collectively contain the sequence where the antigenic epitopes have been already found (for example, peptide 5, or 6 or 22, or 23, or 13, etc.). Antigenic activity of each short peptide from the set is analyzed by the procedures described herein. Immunoreactive regions of 6 aa long (or 7 aa, or 8 aa, etc.) are used to design other peptides of 5 aa long which are overlapped by 4 aa regions. If the antigenic activity remains in the peptides, a set of shorter peptides of 4 aa long is synthesized. All peptides are comparatively analyzed to find the best peptide sequences strongly and specifically immunoreactive with anti-HEV antibody. These peptides could also be used in a mixture to detect anti-HEV antibody.

TABLE 1

PRIMARY AND PREDICTED SECONDARY STRUCTURE FOR SELECTED REGIONS OF THE PROTEIN ENCODED BY ORF2 OF HEV GENOME

| Peptide | Position | Primary and secondary structure | |
|---|---|---|---|
| 7 | 54–65 | PYIHPTNPFAPD<br>sssstttttccc | (SEQ ID NO:14) |
| 9 | 84–101 | GSAWRDQAQRPAVASRRR<br>cccccccccctttcccccc | (SEQ ID NO:15) |
| 19 | 312–329 | TPGNTNTRVSRYSSTARH<br>cttttcccccccccccccc | (SEQ ID NO:20) |
| 11 | 319–340 | RVSRYSSTARHRLRRGADGTAE | (SEQ ID NO:5) |

TABLE 1-continued

PRIMARY AND PREDICTED SECONDARY STRUCTURE FOR SELECTED REGIONS OF THE PROTEIN ENCODED BY ORF2 OF HEV GENOME

| Peptide | Position | Primary and secondary structure | |
|---|---|---|---|
| | | cccccccccccccccccccccc | |
| 33 | 415-433 | TSVENAQQDKGIAIPHDIDL | (SEQ ID NO:12) |
| | | sssttttsssssssstttss | |
| 12 | 422-437 | DKGIAIPHDIDLGESR | (SEQ ID NO:6) |
| | | cttsssttccttttc | |
| 13 | 442-460 | DYDNQHEQDRPTPSPAPSR | (SEQ ID NO:7) |
| | | ccccccccccccccccttc | |
| 14 | 479-492 | EYDQSTYGSSTGPV | (SEQ ID NO:16) |
| | | cccccctttctttts | |
| 15 | 521-534 | LDGRPLSTIQQYSK | (SEQ ID NO:17) |
| | | sccctttcccttt | |
| 17 | 612-634 | DTLDYPARAHTFDDPCPECRPLG | (SEQ ID NO:18) |
| | | ccccctttccccccccttttttt | |
| 40 | 562-580 | NTTASDQLLVENAAGHRVA | (SEQ ID NO:13) |
| | | sstttcsssssttttccss | |
| 22 | 631-648 | RPLGLQGCAFQSTVAELQ | (SEQ ID NO:8) |
| | | ctttcccccccccchhhhh | |
| 23 | 641-660 | QSTVAELQRLKMKVGKTREL | (SEQ ID NO:9) |
| | | ccchhhhhhhccccccccc | |

Elements of secondary structure are indicated as follow: h — alpha-helix; s — beta-sheet; t — beta-turn; c — random coil

TABLE 2

PRIMARY AND PREDICTED SECONDARY STRUCTURE FOR THE SELECTED REGIONS OF THE PROTEIN ENCODED BY ORF3 OF HEV GENOME

| Peptide | Position | Primary and secondary structure | |
|---|---|---|---|
| 2 | 31-40 | CPRHRPVSRL | (SEQ ID NO:3) |
| | | stttctttcs | |
| 3 | 63-76 | SPSQSPIFIQPTPSG | (SEQ ID NO:4) |
| | | stttssssscccc | |
| 4 | 73-87 | PTPSPPMSPLRPGLD | (SEQ ID NO:19) |
| | | cccctttcttcttss | |
| 5 | 91-110 | ANPPDHSAPLGVTRPSAPPLA | (SEQ ID NO:1) |
| | | ccttcccctttccccttcccc | |
| 6 | 105-123 | PSAPPLPHVVDLPQLGPRR | (SEQ ID NO:2) |
| | | ttcccccccccctttcccc | |
| 28 | 91-110 | ANQPGHLAPLGEIRPSAPPLA | (SEQ ID NO:10) |
| | | ccttcccctttccccttcccc | |
| 29 | 105-123 | PSAPPLPPVADLPQPGLRR | (SEQ ID NO:11) |
| | | ttccccccccccttcccc | |

Elements of secondary structure are indicated as follow: h — alpha-helix; s — beta-sheet; t — beta-turn; c — random coil
Peptides 28 and 29 represent the protein encoded by ORF3 of Mexico strain HEV (Yarbough et al., 1991).

TABLE 3

IDENTIFICATION OF SYNTHETIC PEPTIDES SPECIFICALLY REACTIVE WITH SERA FROM PATIENTS INFECTED WITH HEPATITIS E VIRUS
(Central Asia, 1985)

| PEP-TIDE | SERA POSITIVE BY WESTERN BLOT | | | | | | | NEGATIVE SERA | | |
|---|---|---|---|---|---|---|---|---|---|---|
| | TOTAL | +++ | ++ | + | W+ | – | (+) % | TOTAL | + | – |
| 2 | 33 | 2 | 3 | 5 | 0 | 23 | 30.3 | 26 | 1 | 25 |
| 3 | 32 | 2 | 1 | 5 | 1 | 23 | 28.1 | 27 | 0 | 27 |
| 4 | 12 | 0 | 0 | 0 | 0 | 12 | 0 | 9 | 0 | 9 |
| 5 | 40 | 25 | 9 | 1 | 4 | 1 | 97.5 | 27 | 0 | 27 |
| 6 | 40 | 24 | 9 | 0 | 6 | 1 | 97.5 | 27 | 0 | 27 |
| 7 | 5 | 0 | 0 | 0 | 0 | 5 | 0 | 3 | 0 | 3 |
| 9 | 13 | 0 | 0 | 0 | 0 | 13 | 0 | 9 | 0 | 9 |
| 10 | 13 | 0 | 0 | 0 | 1 | 12 | NS | 9 | 1 | 8 |
| 11 | 33 | 2 | 3 | 3 | 2 | 23 | 30.3 | 26 | 1 | 25 |
| 12 | 39 | 3 | 3 | 4 | 2 | 27 | 30.8 | 26 | 0 | 26 |
| 13 | 13 | 0 | 1 | 0 | 0 | 12 | NS | 8 | 3 | 5 |
| 14 | 8 | 0 | 0 | 0 | 1 | 7 | NS | 12 | 1 | 11 |
| 15 | 12 | 0 | 0 | 0 | 0 | 12 | 0 | 9 | 0 | 9 |
| 17 | 25 | 0 | 0 | 0 | 0 | 25 | 0 | 18 | 0 | 18 |
| 19 | 13 | 0 | 0 | 0 | 0 | 13 | 0 | 9 | 0 | 9 |
| 22 | 7 | 2 | 0 | 0 | 0 | 5 | 28.6 | 5 | 0 | 5 |
| 23 | 7 | 2 | 1 | 0 | 0 | 4 | 42.9 | 5 | 0 | 5 |

POSITIVES:
+++ with P/N > 10
++ with P/N = 5-10
+ with P/N = 3-4.9
W+ with P/N = 2.1-2.9
NS — non-specific

TABLE 4

SEROLOGIC ASSAY FOR THE DETECTION OF HEV INFECTION
(Mexico, 1986)

| SAMPLE | PEPTIDE EIA | | | | | | IFA(*) | W/B |
|---|---|---|---|---|---|---|---|---|
| | 5 | 6 | 22 | 23 | 28 | 29 | | |
| 6 | +++ | +++ | ND | ND | ND | ND | + | + |
| 7 | +++ | +++ | ND | ND | ND | ND | + | + |
| 11 | – | – | – | – | – | – | – | – |
| 15 | + | + | – | +++ | + | – | + | + |
| 19 | +++ | +++ | +++ | +++ | +++ | – | + | + |

TABLE 4-continued

SEROLOGIC ASSAY FOR THE DETECTION OF HEV INFECTION
(Mexico, 1986)

| SAMPLE | PEPTIDE EIA | | | | | | IFA(*) | W/B |
|---|---|---|---|---|---|---|---|---|
| | 5 | 6 | 22 | 23 | 28 | 29 | | |
| 66 | + | + | ++ | ++ | + | + | + | + |
| 67 | ++ | ++ | + | − | − | − | − | − |
| 68 | − | − | − | − | − | − | − | − |
| 73 | +++ | +++ | + | +++ | +++ | + | + | + |
| 75 | + | + | + | ++ | + | + | + | + |
| 390 | +++ | +++ | − | − | − | − | + | + |
| 395 | − | − | − | − | − | − | + | + |
| 397 | + | + | + | +++ | +++ | +++ | + | + |
| 399 | − | − | − | − | + | + | + | + |

POSITIVES:
+++ with P/N > 10
++ with P/N = 5–10
+ with P/N = 3–4.9
(*)Fluorescent antibody blocking assay

TABLE 5

REPORTED CASES OF HEV INFECTION
(Kenya, 1991)

| SAMPLE | WESTERN BLOT | | PEPTIDE EIA | | | | | |
|---|---|---|---|---|---|---|---|---|
| | IgG | IgM | 5 | 6 | 22 | 23 | 28 | 29 |
| 40 | + | + | + | + | + | + | − | − |
| 55 | + | + | + | + | + | + | − | − |
| 68 | + | + | + | + | + | + | − | − |
| 69 | + | − | + | + | + | + | − | − |
| 70 | + | + | + | + | + | + | − | − |
| 71 | + | − | + | + | − | + | + | − |
| 72 | + | + | + | + | + | + | − | − |
| 74 | + | + | + | + | + | + | + | − |
| 75 | + | + | + | + | + | + | − | − |
| 83 | + | + | + | + | + | + | − | − |
| 94 | + | − | + | + | − | − | − | − |
| 95 | + | − | + | + | − | + | − | − |
| 96 | + | − | + | + | − | − | + | − |
| 97 | + | + | + | + | + | − | − | − |
| 99 | + | + | + | + | − | + | − | − |
| 100 | + | + | − | − | + | + | − | − |
| 105 | + | − | − | − | + | + | − | − |
| 116 | + | + | + | + | + | + | − | ND |
| 122 | + | + | − | − | + | + | − | ND |
| 128 | + | + | − | − | + | + | − | ND |
| 144 | − | − | − | − | + | − | − | ND |
| 110 | + | + | ND | ND | + | − | + | ND |
| 161 | + | + | + | + | − | + | − | ND |

TOTAL: 23 cases

TABLE 6

SAMPLES POSITIVE FOR SEROLOGIC MARKERS OF HEV
INFECTION WITHOUT HISTORY OF JAUNDICE
(Kenya, 1991)

| Sample | Western blot | | PEPTIDE EIA | | | | | |
|---|---|---|---|---|---|---|---|---|
| | IgG | IgM | 5 | 6 | 22 | 23 | 28 | 29 |
| 29 | + | + | − | − | + | + | − | − |
| 30 | + | − | + | + | + | + | + | − |
| 32 | + | − | − | − | − | − | − | − |
| 35 | + | − | − | − | + | + | − | − |
| 36 | + | − | + | + | − | − | − | − |
| 37 | + | + | − | − | + | + | − | − |
| 39 | + | − | + | + | − | + | − | − |
| 47 | + | − | − | − | + | + | − | − |

TABLE 6-continued

SAMPLES POSITIVE FOR SEROLOGIC MARKERS OF HEV
INFECTION WITHOUT HISTORY OF JAUNDICE
(Kenya, 1991)

| Sample | Western blot | | PEPTIDE EIA | | | | | |
|---|---|---|---|---|---|---|---|---|
| | IgG | IgM | 5 | 6 | 22 | 23 | 28 | 29 |
| 48 | + | − | + | + | + | + | + | − |
| 50 | + | − | + | + | − | − | − | − |
| 79 | + | − | − | − | − | + | − | − |
| 80 | + | + | − | − | − | + | − | − |
| 81 | − | − | − | − | − | + | − | − |
| 82 | + | − | + | + | − | − | − | − |
| 86 | − | + | − | − | − | − | − | − |
| 87 | − | − | − | − | + | + | − | − |
| 88 | − | − | − | − | + | + | − | − |
| 93 | + | + | − | − | + | + | − | − |
| 102 | − | − | − | − | + | − | − | − |
| 103 | + | + | − | − | + | − | − | − |
| 106 | + | + | + | + | + | + | + | − |
| 107 | + | + | + | + | + | − | − | ND |
| 113 | + | + | − | − | + | + | − | ND |
| 115 | + | − | − | − | + | + | − | ND |
| 117 | + | − | − | − | − | − | − | ND |
| 118 | + | − | + | + | + | − | − | ND |
| 119 | − | − | − | − | + | + | − | ND |
| 123 | + | − | − | − | + | + | − | ND |
| 124 | + | + | − | − | + | + | − | ND |
| 133 | − | + | − | − | + | − | − | ND |
| 138 | − | − | + | + | − | + | − | ND |
| 140 | + | + | − | − | − | + | − | ND |
| 142 | + | + | + | + | + | + | − | ND |
| 146 | + | + | + | + | + | + | − | ND |
| 149 | − | − | − | − | + | − | − | ND |
| 152 | + | − | + | + | + | − | − | ND |
| 159 | + | − | + | + | + | − | − | ND | total: 37 samples

TABLE 7

Anti-HEV Activity by Peptide EIA
Percent positivity by region and source of specimen

| Region | Source of specimen | Total | Anti-HEV positive No. (%) |
|---|---|---|---|
| Tadgikistan | outbreak | 64 | 63 (98.4%) |
| Tadgikistan | healthy population | 639 | 41 (6.4%) |
| Kergistan | outbreak | 82 | 70 (85.4%) |
| Mexico | outbreak | 38 | 32 (84.2%) |
| U.S.A. (sentinel counties) | sporadic | 39 | 0 |
| Montana, USA | HAV/outbreak | 283 | 1 (0.35%) |
| Russia | HBV | 38 | 0 |
| Russia | HDV | 25 | 0 |
| Russia | HCV | 25 | 0 |

EXAMPLE 2

Enzyme Immunoassay for the Detection of Anti-HEV Activity Based on Synthetic Peptides Seventeen synthetic peptides based on the Burma strain of HEV and encoded in ORF2 and ORF3 were first used individually for the identification of immunoreactive epitopes as described above (Table 3). Eight of these peptides contained important immunodiagnostic epitopes when tested against sera obtained from HEV infected individuals. Peptides 5 and 6 corresponding to the C-terminus of ORF3 identified more than 90% of acute-phase sera (Table 3) and approximately 30% of convalescent-phase sera (data not shown). Other synthetic peptides when tested individually yielded lower rates of reactivity compared to peptides 5 and 6, or demonstrated non-specific reactions. Consequently, various mixtures of synthetic peptides were examined on the solid-phase.

To ascertain the diagnostic significance of various mixtures of synthetic peptides, each mixture was tested against a panel of sera. This panel was composed of 45 acute-phase specimens (1–10 days after onset of jaundice) obtained from an HEV outbreak in an endemic region of Central Asia, and 14 follow-up convalescent-phase specimens (4–6 mos after onset of jaundice) from these patients. In addition, 36 sera obtained from a normal donor population from a non-endemic region were used as negative controls. Each specimen was diluted in normal goat serum buffer (NGS-Buff) composed of 0.01M PBS, pH 7.2–7.4, containing 10% normal goat serum (NGS), 1% bovine serum albumin (BSA), and 0.05% Tween 20. Anti-HEV activity in each member of the panel was ascertained by WB analysis (Favorov et al. *J. Med. Virol.*, 1992). All acute-phase and convalescent-phase sera tested positive by WB, while all the donor sera were negative by WB.

The panel described above was not only used to assess different combinations of synthetic peptides adsorbed to the solid-phase, but also used to assess the sensitivity and specificity of the peptide-EIA by ascertainment of positivity among the acute- and convalescent-phase sera, and among the normal donor population sera, respectively.

Three different approaches were used to configure various mixtures of synthetic peptides adsorbed to the solid-phase.
Unconjugated Peptide Mixtures.

The first approach (mixtures 1–5) was composed of only unconjugated synthetic peptides in various concentrations. The results of each mixture were empirically obtained and mixture 5 adsorbed to the solid-phase yielded the best results. This mixture was composed of the following synthetic peptides: #6 (20 ug/ml), #5 (10 ug/ml), #11 (5 ug/ml), #12 (1 ug/ml), #22 (1 ug/ml), #23 (5 ug/ml), #28 (2 ug/ml), and #29 (2 ug/ml). Peptides #28 and #29 are based on the Mexico strain of HEV, as described above, and correspond to the exact nucleotide position of peptides #5 and #6. The frequency of anti-HEV using mixture 5 was $41/45$ (91.1%) among acute-phase sera, $12/14$ (85.7%) among convalescent-phase sera, $3/36$ (8.3%) among normal donor sera. The 8.3% positivity value was considered the result of false-positive reactions.
Individual Peptides Conjugated to BSA.

The second approach involved conjugating BSA to individual synthetic peptides. Peptides were conjugated to BSA using 1-ethyl-3-(3-dimethylaminopropyl)carbodiimide hydrochloride (EDC) (Pierce Chemical Co., Rockford, Ill.) according to the method of Bauminger and Wilchek (15). Briefly, 10 mg of individual synthetic peptide or a mixture of peptides was dissolved in distilled water at a final concentration of 1 mg/ml. EDC crystals were added to the peptide solution at a final concentration of 10 mg/ml and the pH was adjusted to 5.0. The reaction mixture was incubated at room temperature for 5 min and BSA was added to yield a final molar ratio of approximately 1 mole of peptide to each 10 amino acids of BSA. The reaction mixture was further incubated at room temperature for 4 hours. The conjugation reaction was stopped by adding sodium acetate, pH 4.2, to a final concentration of 100 mM and the reaction mixture was incubated at room temperature for an additional 1 hour. The peptide-protein conjugate was separated from the remaining peptide and other reaction products by dialysis against 0.01M phosphate buffered saline, pH 7.2, overnight at 4° C. The peptide-protein conjugate was stored in the same buffer at −20° C. This protocol will work for other peptides regardless of sequence.

Conjugates were diluted in normal goat serum buffer (NGS-Buff) composed of 0.01M PBS, pH 7.2–7.4, containing 10% normal goat serum (NGS), 1% bovine serum albumin (BSA), and 0.05% Tween 20. This buffer was also used for the development of a neutralization test (Neut-Buff).

After conjugation various concentrations of conjugated peptides (mixtures 1–7) were mixed and adsorbed to the solid-phase. The optimal results were obtained with mixture 7 and was determined empirically. This mixture was composed of the following conjugated peptides: #23 (20 ug/ml), #6 (14 ug/ml), #5 (8 ug/ml), #22 (4 ug/ml), and #13 (4 ug/ml). The frequency of anti-HEV using mixture 7 was $44/45$ (97.8%) among acute-phase sera, $12/14$ (85.7%) among convalescent-phase sera, and $1/36$ (2.8%) among normal donor sera. This specimen was considered a false-positive reaction. Although peptide #13 demonstrated significant non-specific reactions when tested unconjugated (Table 1), after conjugation to BSA this non-specific reaction disappeared based on comparison of mixtures 5 and 7.
Peptide Mixtures Conjugated to BSA.

The third approach involved conjugating a mixture of the same concentrations of synthetic peptides as indicated above in mixture 7 to BSA (mixture 9). In this way, theoretically, each epitope was represented on each molecule of BSA and resulted in the synthesis of an artificial antigen complex that may approximate the immunoreactivity of the natural antigen. In addition, such a complex may allow for a more uniform distribution of antigenic epitopes on the solid-phase. Using mixture 9, $45/45$ acute-phase sera were positive for anti-HEV activity, $13/14$ convalescent-phase sera were positive, while all normal donor sera remained negative.
Peptide-EIA.

Immulon II EIA microtiter wells (Dynatech Laboratories, Inc. Chantilly, Va.) were adsorbed with 105 ul of individual peptides or conjugated peptides overnight at room temperature. After adsorption, each well was washed 5 times with deionized H2O containing 0.5% Tween 20. Each specimen was then diluted appropriately in NGS-Buff and 100 ul of the diluted specimen was added to each well. Following an incubation period of 1 hr at 37° C., each well was washed 7 times, and 100 ul of diluted conjugate was added to each well. The wells were then incubated again for 1 hr at 37° C., washed 7 times, and 100 ul of substrate solution (o-phenylenediamine and H2O2 obtained from Abbott Laboratories) was added. The wells were incubated for 15–30 min at room temperature in the dark, after which the enzyme reaction was stopped with 50 ul of 1N H2SO4. The wells were read in an ELISA reader set at an optical density of 493 nm. The cutoff value for a positive result was statistically determined based on a frequency distribution of 480 WB positive and negative sera.

To assess the individual antigenic immunologic activity of three out of five epitopes in mixture 9 adsorbed to the solid-phase, serial 2-fold dilutions of individual guinea pig anti-peptide #23, #6 and #5 were added to the solid-phase and incubated. After a wash cycle, goat anti-guinea pig IgG conjugated to HRP was used to detect antigenic epitope activity on the solid-phase. As a control, guinea pig anti-peptide #28 was similarly diluted and tested with mixture 9, which is devoid of peptide #28 activity. The endpoint of each anti-peptide serum exceeded a dilution of 1:32,000 indicating that these epitopes were immunologically active and accessible in mixture 9 after adsorption to the solid-phase, while the negative control remained unreactive at each dilution.

Frequency Distribution.

To determine the utility of the peptide-EIA to discriminate between positive and negative sera, 483 sera were selected and tested at a 1:100 dilution against mixture 9 and a frequency distribution was constructed (FIG. 2). The frequency distribution revealed that three zones could be defined; namely, a positive zone, a negative zone, and an indeterminate zone. The cutoff for the positive zone was equal to the mean of negative controls plus 6.3 standard deviations (SD) of the mean. Optical density values below 0.07 (mean plus 3.9 SD or mean times 3.2) were considered in the negative zone, while optical density values greater than 0.07 and less than 0.10 were considered in the indeterminate zone. Three specimens yielded indeterminate values. Upon retesting at a 1:10 dilution, these sera tested positive for anti-HEV activity.

Neutralization Assay.

A neutralization test was developed to confirm anti-HEV activity in sera. Briefly, follow the above protocol for peptide EIA, but incubate the specimen with mixture 5 (individual unconjugated peptides) before adding to mixture 9; remove the specimen incubated with mixture 5 and add it to absorbed mixture 9. This test is particularly important for those specimens that yielded optical density values close to the cutoff value and for those specimens that yielded optical density values within the indeterminate zone. The use of a neutralization test significantly lowered the false-positivity rate, especially in sera which have been improperly stored or which have undergone several freeze-thaw cycles. The neutralizing agent must be different from the peptide or peptide mixture adsorbed to the solid-phase; otherwise, false-positive reactions would be incorrectly neutralized leading to confirming a truly negative specimen as being positive. Thus, individual synthetic unconjugated peptides were used as the neutralizing agent by incubating the diluted specimen at 37° C. for 1 hr in a fluid-phase before addition to the well containing adsorbed mixture 9. After testing various concentrations, the optimal concentration of each synthetic unconjugated peptide was as follows: #23 (40 ug/ml), #6 (30 ug/ml), #5 (15 ug/ml), #22 (10 ug/ml), #13 (10 ug/ml).

FIG. 3 presents the results of a neutralization test using sera which initially tested positive and yielded optical density values from 0.1 to greater than 2.5. Sera were confirmed as positive when the optical density values were decreased by 50% following incubation with the neutralizing mixture. With the exception of sera that gave OD values greater than 2.5, all sera were confirmed as positive with mean neutralization activities ranging from between 63% to 78%. Sera that yielded OD values greater than 2.5 were retested at a higher dilution at of 1:500. All sera were successfully neutralized after dilution.

The final design of the peptide-EIA involves testing each specimen for anti-HEV activity simultaneously with and without neutralization at an initial dilution of 1:50. The first row of the microtiter wells contains sera diluted in NGS-buff and the second row contains diluted and neutralized sera so that the same sera are located in two wells in a vertical position. Initially reactive but non-neutralized sera which yielded OD values greater 2.0 were retested at a 1:100 dilution. In addition, sera that yielded OD values greater than 2-times the mean of negative controls and that were not neutralized were retested at a 1:10 dilution. These sera were considered to be positive for anti-HEV activity if the OD values were reduced by 50% following neutralization.

Endpoint Determinations.

Following the final design of the peptide-EIA, endpoint determinations were made on thirty-three sera with OD values greater than 2.0. Most of these sera demonstrated an endpoint titer of 1:1000 to 1:10,000. Three sera within this group demonstrated endpoint titers exceeding 1:100,000 (data not shown).

Anti-HEV Activity by Region and Source.

The peptide-EIA using mixture 9 was used to determine anti-HEV activity in sera collected from various regions of the world and included sera from HEV outbreaks in two HEV endemic areas (Tadgikistan and Kergizstan, central Asia republics, former USSR; and Mexico), sera from a healthy population obtained from an HEV endemic region (Tadgiskistan), and sera from an HEV non-endemic area (USA) (Table 7). The Montana collection represented a case controlled investigation of an HAV outbreak. In addition, acute-phase sera obtained from Russia positive for markers of HBV, hepatitis delta virus (HDV), and HCV were used as controls. None of the controls demonstrated anti-HEV activity indicating that the peptide-EIA did not falsely identify these sera as past HEV infections. Only one serum in the Montana collection was repeatedly positive (confirmed by neutralization) for anti-HEV activity and remained positive when a follow-up specimen was obtained two years later. The sentinel county specimens represent acute-phase sera collected from an active surveillance system implemented in 4 geographically distinct counties in the USA. The 39 sera were diagnosed as NABCH without any evidence of chronic sequelae on follow-up. All of these sera were negative for anti-HEV activity indicating, with the exception of the single positive serum in Montana, HEV infection in the USA is a rare event, excluding infections acquired upon travel to an endemic region of the world.

Among 639 sera collected from healthy individuals in an HEV endemic region, 41 (6.4%) demonstrated anti-HEV activity indicating prior exposure to HEV. This value represents HEV background of infection in a healthy population in an endemic region of the world.

Finally, in two outbreaks of HEV in the central Asian republic of the former USSR, Tadgiskistan and Kergistan, 98.4% and 85% of the sera were positive for anti-HEV activity, respectively. Collectively, these data show that the peptide-EIA for the detection of anti-HEV is highly specific and sensitive.

Throughout this application various publications are referenced. The disclosures of these publications in their entireties are hereby incorporated by reference into this application in order to more fully describe the state of the art to which this invention pertains. Any incomplete citations referenced above can be found in the following reference list.

REFERENCES

Balayan MS, Andjaparidze, Savinskaya SS, et al. Evidence for a virus in non-A, non-B hepatitis via the fecal-oral route. Intervirology 1983;20:23–31.

Barany, G., and Merrifield. (1980). Solid-phase peptide synthesis. In "The peptides" (E. Gross and J. Meienhofer, Eds.) 1, 1–284. Academic Press, NY.

Bradley DW, Krawczynski K, Cook EH, et al. Enterically transmitted non-A, non-B hepatitis: serial passage of disease in cynomolgus macaques and tamarins and recovery of disease-associated 27-to 34-nm viruslike particles. PNAS USA 1987;84:6277–6281.

Bradley, D. W. (1990a). Hepatitis non-A, non-B viruses become identified as hepatitis C and E viruses. Prog. Med. Virol. 37, 101–135.

Bradley, D. W. (1990b). Enterically-transmitted non-A, non-B hepatitis. British Medical Bulletin 46, 442–461 CDC (1987a). Enterically transmitted non-A, non-B hepatitis—East Africa. MMWR 36, 241–244. CDC (1987b). Enterically Transmitted non-A, non-B hepatitis—Mexico. MMWR 36, 597–602.

Bauminger S, Wilchek M. The use of carbodiimides in the preparation of immunizing conjugates. Methods Enzymol 1980;70:151–159.

Chou, P. Y., and Fasman, G. D. (1978). Empirical predictions of protein conformation. Ann. Rev. Biochem. 47, 251–276.

Eisenberg, D., Schwarz, E., Kamaromy, M., and Wall, R. (1984). Analysis of membrane and surface protein sequences with the hydrophobic moment plot. J. Mol. Biol. 179, 125–142.

Favorov, M. O., Fields, H. A., Purdy, M. M. et al. (1992). Serologic identification of hepatitis E virus infections in epidemic and endemic settings. J. Med. Virol. 36, 246–250.

Goldsmith, R., Yarbough, P. O., Reyes, G. R., et al. (1992). Enzyme-linked immunosorbent assay for diagnosis of acute sporadic hepatitis E in Egyptian children. Lancet 339, 328–331.

Harada, S., Watanabe, Y., Takeuchi, K. et al. (1991). Expression of processed core protein of hepatitis C virus in mammalian cells. J. Virol. 65, 3015–3021.

Ichikawa, M., Araki, M., Rikihisa, T. et al. (1991). Cloning and expression of cDNAs from enterically-transmitted non-A,non-B hepatitis virus. Microbiol. Immunol. 35, 535–543.

Karplus, P. A., and Schulz, G. E. (1985). Prediction of chain flexibility in proteins: a tool for selection of peptide antigens. Naturwissenschaften 72, 212–213.

Khuroo MS. Study of an epidemic on non-A, non-B hepatitis: possibility of another human hepatitis virus distinct from post-transfusion non-A, non-B type. Am J Med 1980;68:818–824.

Klein, P., Kanehisa, M., and DeLisa, C. (1985). The detection and classification of membrane-spanning proteins. Biochem. Biophys. Acta 815, 468–476.

Krawczynski, K., and Bradley, D. W. (1989). Enterically transmitted non-A, non-B hepatitis: Identification of virus-associated antigen in experimentally infected cynomolgus macaques. J. Infect. Dis. 159, 1042–1049.

Kyte, J. and Doolittle, R. F. (1982). A simple method for displaying the hydropathic character of a protein. J. Mol. Biol. 157, 105–132.

Ptitsyn, O. B., and Finkrlstein, A. V. (1983). Theory of protein secondary structure and algorithm of its prediction. Biopolymers 22, 15–25.

Purcell RH, Ticehurst JR. Enterically transmitted non-A, non-B hepatitis: epidemiology and clinical characteristics. In: Zuckerman AJ, ed. Viral hepatitis and liver disease. New York: Alan R. Liss, 1988:131–137.

Purdy, M., McCaustland, A., Krawczynski, K., et al. (1992). Expression of a hepatitis E virus (HEV)-trpE fusion protein containing epitopes recognized by antibodies in sera from human cases and experimentally infected primates. J. Arch. Virol. in press.

Reyes GR, Purdy MA, Kim JP et al. Isolation of a cDNA from the virus responsible for enterically transmitted non-A, non-B hepatitis. Science 1990;247:1335–1339.

Reyes, G. R., Huang, C. C., Yarborough, P. O., et al. (1991a). Hepatitis E Virus (HEV): Epitope mapping and detecting of strain variation. In "Viral Hepatitis C, D, E" (T. Shikata, R. H. Purcell, T. Uchida, Ess.), pp.237–245. Elsevier Science Publishers, NY.

Reyes, G. R., Yarbough, P. O., Tam, A. W., et al. (1991b). Hepatitis E virus (HEV): The novel agent responsible for enterically transmitted non-A, non-B hepatitis. Gastroenterologia Japonica 26 (suppl.3), 142–147.

Tam, A. W., Smith, M. M., Guerra, M. E., et al. (1991b). Hepatitis E virus (HEV): Molecular cloning and sequencing of the full-length viral genome. Virology 185, 120–131.

Tassopoulos, N. C., Koutelou, M. G., Macagno, S. et al. (1990). Diagnostic significance of IgM antibody to hepatitis delta virus fulminant hepatitis B. J. Med. Virol. 30, 174–177.

Vishwanathan, R. (1957). Infectious hepatitis in Delhi (1955–56). Indian J. Med. Res. (Suppl.) 45, 1–30.

Wang, Q. H., Lu, Z. M., Wang, Y. Q., and Chen, M. J. (1985). Diagnostic significance of IgM anti-HBc detection by ELISA in HBV infection. Chin. Med. J. 98, 703–707.

Wong DC, Purcell RH, Screenivasan MA, SR Prasad, KM Pavri. Epidemic and endemic hepatitis in India: evidence for a non-A, non-B hepatitis virus aetiology. Lancet 1980; ii:876–879.

Wright, R. (1990). Viral hepatitis comparative epidemiology. British Medical Bulletin 46, 549–558.

Yarbough, P. O., Tam, A. W., Fry, K. E., et al. (1991). Hepatitis E virus: Identification of type-common epitopes. J. Virol. 65, 5790–5797.

Zuckerman AJ. Hepatitis E virus: the main cause of enterically transmitted non-A, non-B hepatitis. Br Med J 1990;300:1475–1476.

---

What is claimed is:

1. An antigenic peptide having a sequence consisting of the amino acids contained in the amino acid sequence defined in the Sequence Listing by SEQ ID NO:1.

2. An antigenic peptide having a sequence consisting of the amino acids contained in the amino acid sequence defined in the Sequence Listing by SEQ ID NO:3.

3. An antigenic peptide having a sequence consisting of the amino acids contained in the amino acid sequence defined in the Sequence Listing by SEQ ID NO:4.

4. An antigenic peptide having a sequence consisting of the amino acids contained in the amino acid Sequence defined in the Sequence Listing by SEQ ID NO:5.

5. An antigenic peptide having a sequence consisting of the amino acids contained in the amino acid sequence defined in the Sequence Listing by SEQ ID NO:6.

6. An antigenic peptide having a sequence consisting of the amino acids contained in the amino acid sequence defined in the Sequence Listing by SEQ ID NO:7.

7. An antigenic peptide having a sequence consisting of the amino acids contained in the amino acid sequence defined in the Sequence Listing by SEQ ID NO:8.

8. An antigenic peptide having a sequence consisting of the amino acids contained in the amino acid sequence defined in the Sequence Listing by SEQ ID NO:9.

9. An antigenic peptide having a sequence consisting of the amino acids contained in the amino acid sequence defined in the Sequence Listing by SEQ ID NO:12.

10. An antigenic peptide having a sequence consisting of the amino acids contained in the amino acid sequence defined in the Sequence Listing by SEQ ID NO:13.

11. An antigenic composition comprising antigenically effective amounts of at least two different peptides, wherein the peptides have a sequence consisting of the amino acids contained in the amino acid sequences defined in the Sequence Listing by SEQ ID NO:1 and SEQ ID NO:2.

12. An antigenic composition comprising at least four different peptides, wherein the peptides have a sequence consisting of the amino acids contained in the amino acid sequences defined in the Sequence Listing by SEQ ID NO:1, SEQ ID NO:2, SEQ ID NO:8 and SEQ ID NO:9.

13. The composition of claim 12, wherein each peptide is conjugated to carrier.

14. The composition of claim 12, wherein each peptide is bound to a substrate.

15. The composition of claim 12, further comprising peptide having a sequence consisting of the amino acids contained in the amino acid sequence defined in the Sequence Listing by SEQ ID NO:7.

16. The composition of claim 15, wherein the concentration ratio of the peptides defined by SEQ ID NO:1, SEQ ID NO:2, SEQ ID NO:7, SEQ ID NO:8 and SEQ ID NO:9 is about 8:14:4:4:20.

17. The composition of claim 15, wherein each peptide is conjugated to an carrier.

18. The composition of claim 15, wherein each peptide is bound to a substrate.

19. An antigenic composition comprising antigenically effective amounts of at least eight peptides, wherein the peptides have a sequence consisting of the amino acids contained in the amino acid sequences defined in the Sequence Listing by SEQ ID NO:1, SEQ ID NO:2, SEQ ID NO:5, SEQ ID NO:6, SEQ ID NO:8, SEQ ID NO:9, SEQ ID NO:10 and SEQ ID NO:11.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ala  Asn  Pro  Pro  Asp  His  Ser  Ala  Pro  Leu  Gly  Val  Thr  Arg  Pro  Ser
 1              5                        10                       15
```

```
            Ala  Pro  Pro  Leu  Ala
                          20
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Pro  Ser  Ala  Pro  Pro  Leu  Pro  His  Val  Val  Asp  Leu  Pro  Gln  Leu  Gly
1                   5                        10                       15

Pro  Arg  Arg
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Cys  Pro  Arg  His  Arg  Pro  Val  Ser  Arg  Leu
1                   5                        10
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Ser  Pro  Ser  Gln  Ser  Pro  Ile  Phe  Ile  Gln  Pro  Thr  Pro  Ser  Gly
1                   5                        10                       15
```

( 2 ) INFORMATION FOR SEQ ID NO:5:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Arg  Val  Ser  Arg  Tyr  Ser  Ser  Thr  Ala  Arg  His  Arg  Leu  Arg  Arg  Gly
1                   5                        10                       15

Ala  Asp  Gly  Thr  Ala  Glu
                    20
```

( 2 ) INFORMATION FOR SEQ ID NO:6:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Asp  Lys  Gly  Ile  Ala  Ile  Pro  His  Asp  Ile  Asp  Leu  Gly  Glu  Ser  Arg
1              5                        10                           15
```

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Asp  Tyr  Asp  Asn  Gln  His  Glu  Gln  Asp  Arg  Pro  Thr  Pro  Ser  Pro  Ala
1              5                        10                           15

Pro  Ser  Arg
```

( 2 ) INFORMATION FOR SEQ ID NO:8:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Arg  Pro  Leu  Gly  Leu  Gln  Gly  Cys  Ala  Phe  Gln  Ser  Thr  Val  Ala  Glu
1              5                        10                           15

Leu  Gln
```

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Gln  Ser  Thr  Val  Ala  Glu  Leu  Gln  Arg  Leu  Lys  Met  Lys  Val  Gly  Lys
1              5                        10                           15

Thr  Arg  Glu  Leu
               20
```

( 2 ) INFORMATION FOR SEQ ID NO:10:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Ala  Asn  Gln  Pro  Gly  His  Leu  Ala  Pro  Leu  Gly  Glu  Ile  Arg  Pro  Ser
1              5                        10                           15

Ala  Pro  Pro  Leu  Ala
```

20

( 2 ) INFORMATION FOR SEQ ID NO:11:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Pro Ser Ala Pro Pro Leu Pro Pro Val Ala Asp Leu Pro Gln Pro Gly
 1               5                  10                  15
Leu Arg Arg
```

( 2 ) INFORMATION FOR SEQ ID NO:12:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Thr Ser Val Glu Asn Ala Gln Gln Asp Lys Gly Ile Ala Ile Pro His
 1               5                  10                  15
Asp Ile Asp Leu
             20
```

( 2 ) INFORMATION FOR SEQ ID NO:13:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Asn Thr Thr Ala Ser Asp Gln Leu Leu Val Glu Asn Ala Ala Gly His
 1               5                  10                  15
Arg Val Ala
```

( 2 ) INFORMATION FOR SEQ ID NO:14:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Pro Tyr Ile His Pro Thr Asn Pro Phe Ala Pro Asp
 1               5                  10
```

( 2 ) INFORMATION FOR SEQ ID NO:15:

( i ) SEQUENCE CHARACTERISTICS:
        ( A ) LENGTH: 18 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:15:

Gly Ser Ala Trp Arg Asp Gln Ala Gln Arg Pro Ala Val Ala Ser Arg
1               5                   10                  15

Arg Arg ( 2 ) INFORMATION FOR SEQ ID NO:16:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Glu Tyr Asp Gln Ser Thr Tyr Gly Ser Ser Thr Gly Pro Val
1               5                   10

( 2 ) INFORMATION FOR SEQ ID NO:17:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Leu Asp Gly Arg Pro Leu Ser Thr Ile Gln Gln Tyr Ser Lys
1               5                   10

( 2 ) INFORMATION FOR SEQ ID NO:18:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Asp Thr Leu Asp Tyr Pro Ala Arg Ala His Thr Phe Asp Asp Phe Cys
1               5                   10                  15

Pro Glu Cys Arg Pro Leu Gly
                20

( 2 ) INFORMATION FOR SEQ ID NO:19:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Pro Thr Pro Ser Pro Pro Met Ser Pro Leu Arg Pro Gly Leu Asp
1               5                   10                  15

( 2 ) INFORMATION FOR SEQ ID NO:20:

```
( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:20:

Thr Pro Gly Asn Thr Asn Thr Arg Val Ser Arg Tyr Ser Ser Thr Ala
1               5                   10                  15
Arg His
```